United States Patent [19]
Yu et al.

[11] Patent Number: 5,492,935
[45] Date of Patent: *Feb. 20, 1996

[54] COMPOSITIONS COMPRISING RETINAL AND DERIVATIVES THEREOF FOR TREATMENT OF COSMETIC OR DERMATOLOGIC SKIN DISORDERS

[76] Inventors: Ruey J. Yu, 4 Lindenwold Ave., Ambler, Pa. 19002; Eugene J. Van Scott, 3 Hidden La., Abington, Pa. 19001

[ * ] Notice: The term of this patent shall not extend beyond the expiration date of Pat. No. 5,093,360.

[21] Appl. No.: 318,560

[22] Filed: Oct. 5, 1994

Related U.S. Application Data

[60] Continuation of Ser. No. 844,173, Mar. 2, 1992, abandoned, which is a division of Ser. No. 334,518, Apr. 7, 1989, Pat. No. 5,093,360.

[51] Int. Cl.$^6$ .................... A61K 31/075; A61K 31/11; A61K 31/33
[52] U.S. Cl. ............... 514/703; 514/463; 514/467
[58] Field of Search ...................... 514/463, 703

[56] References Cited

U.S. PATENT DOCUMENTS

| | | | |
|---|---|---|---|
| 3,932,665 | 1/1976 | Van Scott et al. | 514/703 |
| 4,034,114 | 7/1977 | Yu et al. | 514/703 |
| 4,877,805 | 10/1989 | Kligman | 514/725 |
| 5,093,360 | 5/1992 | Yu et al. | 514/703 |

FOREIGN PATENT DOCUMENTS

| | | |
|---|---|---|
| 339905 | 11/1989 | European Pat. Off. |
| 901659 | 11/1959 | United Kingdom |

OTHER PUBLICATIONS

Verma et al. Chemical Abstracts vol. 87, 1977 Abstract 111591j.
Connor et al. Chemical Abstracts. vol. 105, 1986 Abstract 599p.
Oikarinen et al. Chemical Abstracts, vol. 103, 1985 Abstract 16837j.
Isakov et al. Chemical Abstracts, vol. 109, 1988 Abstract 142119p.
The Merck Manual (Rahway, N.J., 1987, Merck and Company,) pp. 2301–2302.
Berne et al. Chemical Abstracts, vol. 101, 1984, Abstract 206856w.
Fiedler–Nagy, et al. Chemical Abstracts, vol. 108, 1988, Abstract 31950n.
Yoshioka, et al., Chemical Abstracts, vol. 105, 1986 Abstract 18425p.
Verma et al. Cancer Research 37 2196–2201 1977.
Patent Abstracts of Japan, vol. 9, No. 82, Apr. 11, 1989.
Patent Abstracts of Japan, vol. 13, No. 227, May 25, 1989.
Patent Abstracts of Japan, vol. 10, No. 350, Nov. 26, 1986.

*Primary Examiner*—Mukund J. Shah
*Assistant Examiner*—Pavanaram K. Sripada
*Attorney, Agent, or Firm*—Foley & Lardner

[57] ABSTRACT

Therapeutic as well as preventive measures to improve cosmetic conditions and to alleviate the symptoms of dermatologic disorders with retinal and its derivatives is disclosed. Cosmetic conditions and dermatologic disorders in humans and domestic animals in which retinal and its derivatives may be useful include age spots, wrinkles, warts, eczema, seborrheic keratoses, acne, oily skin, psoriasis, dandruff, xerosis, inflammatory and pruritic skin, disturbed keratinization, skin changes associated with aging and possibly viral infections. Retinal and its derivatives include their stereoisomers, for example, all-trans, 13-cis, 11-cis, 9-cis, 7-cis, 11,13-cis and 9,13-cis vitamin A aldehydes, their hydrate, hemiacetal and acetal forms, and their adduct compounds. Compositions containing retinal or its derivative may be administered systemically such as orally, or topically to the affected areas of the skin.

16 Claims, No Drawings

COMPOSITIONS COMPRISING RETINAL AND DERIVATIVES THEREOF FOR TREATMENT OF COSMETIC OR DERMATOLOGIC SKIN DISORDERS

This application is a continuation of application Ser. No. 07/844,173, filed Mar. 2, 1992, abandon which in turn is a Divisional of application Ser. No. 07/334,518, filed Apr. 7, 1989, now U.S. Pat. No. 5,093,360.

Be it known that Ruey J. Yu, Ph.D., O.M.D. of 4 Lindenwold Avenue, Ambler, Pa. 19002, and Eugene J. Van Scott, M.D. of 3 Hidden Lane, Abington, Pa. 19001, having made an invention entitled: RETINAL, DERIVATIVES AND THEIR THERAPEUTIC USE.

The following disclosure contains a correct and full description of the invention and of the best mode known to the inventors of taking advantage of same.

Topical treatment with retinal and its derivatives has been found to eradicate or improve age spots, wrinkles, warts, oily skin, psoriasis, eczema, dandruff and other skin changes associated with aging. Oral administration of retinal has been found to eradicate or improve acne, psoriasis and other disorders of disturbed keratinization and inflammation.

This invention relates generally to therapeutic treatment as well as preventive measures of cosmetic, dermatologic and other conditions and disorders by either topical or systemic administration of compositions containing retinal or its derivatives. As will be subsequently described in detail, we initially discovered that retinal was effective in the topical treatment of acne, actinic and nonactinic keratoses.

We have now discovered that compositions containing retinal and its derivatives may have much broader ranges of therapeutic actions on topical or systemic administration for various cosmetic, dermatologic and other conditions and disorders in humans and animals.

In our prior patent application entitled "Process for the Treatment of Acne Vulgaris Utilizing Retinal", Ser. No. 458,095, filed Apr. 5, 1974, now U.S. Pat. No. 3,932,665, we described and claimed a method of treating acne vulgaris in humans using topical preparations containing retinal. In our patent application entitled "Treatment of Skin Keratoses with Retinal", Ser. No. 723,327, filed Sep. 15, 1976, now U.S. Pat. No. 4,034,114, we described and claimed a method of treating actinic or nonactinic keratoses in humans using topical preparations containing retinal. The actinic keratoses, also known as solar keratoses are found on the sunlight exposed areas of the body such as on the face, head, neck and hands.

DESCRIPTION OF THE INVENTION

It has now been discovered that retinal and its derivatives can be therapeutically useful on topical or systemic administration against varieties of cosmetic and dermatologic conditions and disorders including oily skin, age spots, wrinkles, warts, acne, eczema, seborrheic keratoses, psoriasis, dandruff, xerosis, inflammatory and pruritic skin, disturbed keratinization, skin changes associated with aging and viral infections.

In accordance with the present invention, retinal and its derivative which are incorporated in therapeutic compositions for topical, oral or other forms of systemic administration to prevent or alleviate the conditions and symptoms of cosmetic and dermatologic disorders are described as follows.

Retinal, also called vitamin A aldehyde is distinctly different in chemistry from retinol and Retinoic acid. Retinol, also called vitamin A alcohol is commonly known as vitamin A, and is present in fish liver oils as an ester compound, retinyl palmitate. Retinoic acid, also called vitamin A acid is an oxidation product from retinol or retinal. Both retinol and retinal are important in the physiologic functions of vision, growth, reproduction and differentiation, but retinoic acid does not contribute to vision and reproduction in humans and animals.

Retinal can exist in stereoisomeric forms, namely all-trans, 13-cis, 11-cis, 9-cis, 7-cis, 11,13-cis, 9,13-cis. However, the common form is all-trans retinal. Since retinal is chemically an aldehyde it can exist as hemiacetal and acetal forms by reacting with one or two molecules of an alcohol, such as methanol, ethanol or propanol. Such hemiacetal and acetal forms are usually more stable against alkali, and are more resistant to oxidation of the aldehyde group. Retinal may be shown by the following chemical structure:

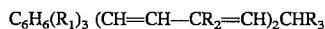

wherein $R_1$, $R_2$=alkyl, aralkyl, aryl or alkoxy group of saturated or unsaturated, straight or branched chain or cyclic form, having 1 to 25 carbon atoms, $R_3$=O or $(OR_4)(OR_5)$, wherein $R_4$, $R_5$=H, alkyl, aralkyl, aryl, diol or polyol group of saturated or unsaturated, straight or branched chain or cyclic form, having 1 to 25 carbon atoms; and the hydrogen atom attached to the carbon atom in the main chain as well as in $R_1$, $R_2$, $R_4$ and $R_5$ may be substituted by a halogen atom or a radical such as a lower alkyl, aralkyl, aryl or alkoxy having 1 to 9 carbon atoms. The hemiacetal and acetal forms are represented by —$CH(OR_4)(OR_5)$ instead of —CHO. The compound may be called retinal hemiacetal when either $R_4$ or $R_5$ is H, and the compound is called retinal acetal when both $R_4$ and $R_5$ are for example alkyls or aralkyls. The compound is called retinal hydrate when both $R_4$ and $R_5$ are H.

Retinal and its derivatives may exist as stereoisomers such as all-trans, 13-cis, 11-cis, 9-cis, 7-cis, 11,13-cis and 9,13-cis forms.

The typical alkyl, aralkyl and aryl groups for $R_1$ and $R_2$ are for example, methyl, ethyl, propyl, isopropyl, butyl, pentyl, octyl, lauryl, stearyl, benzyl and phenyl etc. The halogen atoms are F, Cl, Br and I. The typical alkoxy groups are methoxy and ethoxy. The typical diol groups are glycol, propylene glycol and 1,3-butanediol. The typical polyol groups include glycerol, butanetriol, inositol and alditols; such as erythritol of tetraol, ribitol of pentaol, mannitol and sorbitol of hexaols.

Retinal or its derivative may react with an unsaturated chemical agent such as maleic anhydride, acetylene dicarboxylic acid or its ester, or hydroquinone to form a crystalline molecular complex called an adduct compound.

The representative retinal and its derivatives which may be useful for topical or systemic administration to improve cosmetic conditions or to alleviate dermatologic disorders are listed below:
1. Retinal;
2. Retinal hydrate;
3. Retinal methyl hemiacetal;
4. Retinal ethyl hemiacetal;
5. Retinal propyl hemiacetal;
6. Retinal isopropyl hemiacetal;
7. Retinal butyl hemiacetal;
8. Retinal pentyl hemiacetal;
9. Retinal octyl hemiacetal;
10. Retinal benzyl hemiacetal;
11. Retinal dimethyl acetal;
12. Retinal diethyl acetal;

13. Retinal dipropyl acetal;
14. Retinal diisopropyl acetal;
15. Retinal dibutyl acetal;
16. Retinal dipentyl acetal;
17. Retinal dioctyl acetal;
18. Retinal dibenzyl acetal;
19. Retinal hydroquinone adduct;
20. Retinal maleic anhydride adduct;
21. Retinal acetylene dicarboxylic acid ester adduct;
22. Retinal propylene glycol hemiacetal and acetal;
23. Retinal 1,2-o-isopropylidene glyceryl hemiacetal and acetal;
24. Retinal 3-allyloxy-1, 2-propanediol hemiacetal and acetal;
25. Retinal phytyl hemiacetal;
26. Retinal diphytyl acetal;
27. Retinal dodecyl hemiacetal; and
28. Retinal didodecyl acetal.

Retinal and its derivatives may also be utilized in combination with or as additives to enhance therapeutic effects of other cosmetic or pharmaceutical agents to improve cosmetic conditions or alleviate the symptoms of dermatologic disorder. Cosmetic and pharmaceutical agents include those that improve or eradicate age spots, keratoses and wrinkles eradicating agents; antiacne agents; antibacterials; antiyeast agents; antifungal agents; antiviral agents; antidandruff agents; antidermatitis agents; antipruritic agents; antiinflammatory agents; antihyperkeratolytic agents; antidryskin agents; antipsoriatic agents; antiseborrheic agents; hair conditioners and hair treatment agents; antiaging and antiwrinkle agents; sunscreen agents; antihistamine agents; vitamins; corticosteroids, tanning agents; local anesthetics; hormones; retinoids and other dermatologicals.

Some examples of cosmetic and pharmaceutical agents are clotrimazole, miconazole, salicyclic acid, pramoxine, menthol, retinoic acid, hydrocortisone, hydrocortisone valerate, betamethasone valerate, betamethasone dipropionate, triamcinolone acetonide, fluocinonide, hydroquinone, clobetasol propionate, benzoyl peroxide, crotaminton, 5-fluorouracil, monobenzone, vitam A palmitate, vitamin E acetate and vitamin C.

It has been established through tests in humans that retinal and its derivatives are therapeutically effective for topical, oral, intralesional injection or other systemic treatment of various cosmetic conditions and dermatologic disorders.

Accordingly, it is an object of this invention to provide cosmetic as well as medicinal compositions containing retinal or its derivatives which when topically or systemically administered will substantially improve and alleviate the symptoms of various cosmetic conditions or dermatologic disorders.

It is another object of this invention to provide methods for treating various cosmetic conditions or dermatologic disorders with topical preparations or systemic compositions containing retinal or its derivative.

PREPARATION OF THE THERAPEUTIC COMPOSITIONS

Retinal and its derivatives of the instant invention may be formulated either for topical application or for systemic administration. In the topical preparations retinal and its derivatives may be formulated in aqueous or non-aqueous solution, gel, lotion, cream or ointment containing 0.01 to 5 percent and preferably from 0.01 to 0.5 percent by weight of the total composition. When retinal and its derivatives are formulated in aqueous form, sodium sulfite, sodium bisulfite, sodium metabisulfite or other antioxidants may be added to stabilize retinal and its derivatives in aqueous compositions. Butylated hydroxytoluene (BHT) or butylated hydroxyanisole (BHA), on the other hand, may be added to stabilize retinal and its derivatives in non-aqueous composition. To provide maximal stability of the therapeutic compositions antioxidants of both aqueous and nonaqueous types may also be incorporated into the compositions at the same time. For example, both sodium metabisulfite and BHT may be added to an aqueous acholic solution containing retinal. The concentration of antioxidant may range from 0.01 to 1%.

To prepare a typical aqueous solution, retinal or its derivative is dissolved in a mixture of water, ethanol and propylene glycol in a volume ratio of 30:50:20, respectively. Sodium metabisulfite is then added to the above solution. To prepare a typical non-aqueous solution, retinal or its derivative is dissolved in a mixture of ethanol, isopropyl myristate and squalane in a volume ratio of 70:20:10, respectively. BHT is then added to the above solution. When a combination composition is desired retinyl palmitate and/or hydroquinone, for example is added to the above non-aqueous solution. The preferred concentration of retinyl palmitate ranges from 1 to 5%. The concentration of hydroquinone may range from 1 to 5%, but the preferred concentration is 2% by weight of the total composition.

A typical cream or lotion containing retinal or its derivative is prepared by first dissolving retinal or its derivative in ethanol, acetone, propylene glycol or other solvent. The solution thus prepared is then admixed with commonly available oil-in-water emulsions. BHT or sodium metabisulfite may be added to such emulsions to stabilize retinal or its derivative.

A typical gel composition is formulated by first dissolving retinal or its derivative in a mixture of ethanol, water and propylene glycol in a volume ratio of 50:30:20, respectively. A gelling agent such as hydroxyethylcellulose, hydroxypropylcellulose or hydroxypropylmethylcellulose is then added to the mixture with mixing. The preferred concentration of the gelling agent may range from 0.2 to 2 percent by weight of the total composition.

For oral administration retinal powder is mixed with gelatin powder so that each gelatin capsule may contain from 5 to 100 mg of retinal. For intralesional injection, retinal or its derivative is dissolved in a vehicle such as isopropyl myristate or safflower oil, and the solution in an injection bottle is sterilized under standard conditions.

The following are illustrative examples of formulations and compositions according to this invention. Although the examples utilize only selected formulations useful according to this invention, it should be understood that the following examples are intended to be illustrative and not limiting.

EXAMPLE 1

All-trans retinal 0.2 g is dissolved in a 100 ml mixture prepared from ethanol, water and propylene glycol in a volume ratio of 50:30:20, respectively. Sodium metabisulfite 0.5 g is added to the mixture with stirring. The light yellowish solution thus formulated contains 0.2% retinal as an active ingredient in aqueous solution. To prepare a gel composition, hydroxypropyl cellulose 2 g is added to the above solution with mixing until a uniform consistency is obtained.

EXAMPLE 2

All-trans retinal 0.1 g is dissolved in a 100 ml mixture prepared from ethanol, isopropyl myristate and squalane in a volume ratio of 70:20:10, respectively. BHT 0.1 g is added to the mixture with stirring. The non-aqueous solution thus prepared contains 0.1% retinal as an active ingredient. To prepare a combination with vitamin A palmitate and hydroquinone, retinyl palmitate 3 g and hydroquinone 2 g are added to the above non-aqueous solution with stirring until a uniform yellowish solution is obtained.

EXAMPLE 3

A water-washable cream containing retinal 0.1% as an active ingredient may be formulated as follows. 13-cis Retinal 0.1 g is dissolved in 10 ml ethanol, and the solution thus obtained is mixed with 90 g of an oil-in-water emulsion prepared from petrolatum, glyceryl monostearate, stearyl alcohol, PEG-40 stearate, propylene glycol and water in a weight ratio of 25:5:10:5:10:45, respectively. To prepare a combination with vitamin A palmitate and vitamin E, retinyl palmitate 2 g and alpha tocopheryl acetate 1 g are added to the above cream with mixing until a uniform light yellowish composition is obtained.

EXAMPLE 4

A water-nonwashable lotion containing retinal 0.05% as an active ingredient may be formulated as follows. All-trans retinal 0.05 g is dissolved in 100 g of a lotion prepared from sorbitan trioleate, petrolatum, mineral oil, diisopropyl adipate and isopropyl myristate in a weight ratio of 10:20:10:30:30, respectively. BHA 0.05 g is added to the mixture with stirring. To prepare a combination with vitamin A palmitate and hydroquinone, retinal palmitate 2 g and hydroquinone 2 g are added to the above lotion with stirring until a uniform light yellowish lotion is obtained.

EXAMPLE 5

A combination composition containing retinal, hydroquinone and hydrocortisone 17-valerate is formulated as follows. All-trans retinal 0.1 g, hydroquinone 2 g and hydrocortisone 17-valerate 0.2 g are dissolved in ethanol 10 ml and propylene glycol 5 ml, and the solution thus obtained is mixed with 83 g of commonly available oil-in-water cream containing 0.8% of sodium metabisulfite. Light yellowish cream thus prepared contains 0.1% retinal, 2% hydroquinone and 0.2 % hydrocortisone 17-valerate as active ingredients.

EXAMPLE 6

A combination composition containing retinal, vitamin A palmitate and benzilic acid may be formulated as follows. All-trans retinal 0.1 g, retinyl palmitate 3 g, benzilic acid 3 g and BHT 0.05 g are dissolved in 94 ml of a mixture prepared from ethanol, isopropyl myristate and squalane in a volume ratio of 60:30:10, respectively. The composition thus formulated contains 0.1% retinal, 3% vitamin A palmitate and 3% benzilic acid. A sun screen agent such as octyl p-methoxycinnamate and a corticosteroid such as betametasone dipropionate may also be incorporated into the above composition.

EXAMPLE 7

A combination composition containing retinal, gluconolactone, hydroquinone and elastin may be formulated as follows. All-trans retinal 0.05 g, gluconolactone 8 g, hydroquinone 2 g and soluble elastin 0.2 g are dissolved in 90 ml of a mixture prepared from ethanol, water and propylene glycol in a volume ratio of 40:40:20, respectively. Sodium metabisulfite 0.5 g and BHT 0.02 g are added to the above mixture with stirring. The composition thus formulated contains 0.05% retinal, 8% gluconolactone, 2% hydroquinone and 0.2% elastin as active ingredients.

EXAMPLE 8

A combination composition containing retinal, gluconolactone, hydroquinone, elastin and a sun screen agent may be formulated as follows. All-trans retinal 0.04 g, gluconolactone 5 g, hydroquinone 2 g, soluble elastin 0.1 g and octyl p-methoxycinnamate 3 g are dissolved in 90 ml of a mixture prepared from ethanol, water and propylene glycol in a volume ratio of 50:30:20, respectively. Sodium metabisulfite 0.4 g and BHA 0.02 g are added to the above mixture with stirring. Concentrated ammonium hydroxide may be added to adjust the pH to approximately 4.5. The composition thus formulated contains 0.04% retinal, 5% gluconolactone, 2% hydroquinone, 0.1% elastin and 3% octyl p-methoxycinnamate.

EXAMPLE 9

To prepare a composition for intralesional injection retinal 20 mg is dissolved in 10 ml of safflower oil or isopropyl myristate, and the solution thus obtained in an injection bottle is sterilized under standard conditions. The composition thus prepared contains 0.2% or 2 mg per ml of retinal as an active ingredient.

EXAMPLE 10

For oral administration gelatin capsules containing retinal or its derivative in different doses may be prepared as follows. Retinal powder 1 g is thoroughly mixed with 35 g of gelatin powder USP. Each gelatin capsule size No. 0 filled with this mixture contains 10 mg of retinal as an active ingredient. Gelatin capsules containing 25 mg of retinal in each capsule may also be prepared in the same way but from 1 g of retinal and 14 g of gelatin powder.

EXAMPLE 11

Retinal dimethyl acetal may be synthesized and formulated in a therapeutic composition as follows.

All-trans retinal 100 mg is dissolved in 10 ml of methanol, and concentrated hydrochloric acid 0.04 ml is added to the mixture with stirring. The reaction mixture changes instantly in color from yellowish to greenish. After 10 minutes at room temperature the mixture is adjusted to alkaline with 0.1 ml of triethanolamine while the color of the solution changes back to yellowish. The mixture is evaporated at 40° C. in vacuum to about 2 ml in volume. Ether 10 ml and water 30 ml are added, and the ether layer is separated and washed with 20 ml of water. The ether layer is dried over androus sodium sulfate. After evaporation of ether, yellowish product 95 mg is obtained. Retinal dimethyl acetal thus synthesized is identified by infrared spectroscopy, high performance liquid chromatography and thin-layer chromatograph with a mobility of 0.71 on a solvent system of benzene:methanol 1:1.

Retinal dimethyl acetal 50 mg synthesized from the above procedure is dissolved in 3 ml of acetone, and the solution thus obtained is mixed with 47 g of an oil-in-water emulsion. The composition thus formulated contains 0.1% retinal dimethyl acetal as an active ingredient.

EXAMPLE 12

Retinal diethyl acetal may be synthesized and formulated in a therapeutic composition as follows.

All-trans retinal 95 mg is dissolved in 12 ml of ethanol, and concentrated hydrochloric acid 0.04 ml is added to the mixture with stirring. The reaction mixture changes instantly in color from yellowish to brownish. After 30 minutes at room temperature the mixture is adjusted to alkaline with 0.1 ml of triethanolamine while the color of the solution changes back to orange. The mixture is evaporated at 40° C. in vacuum to about 2 ml in volume. Ether 10 ml and water 30 ml are added, and the ether layer is separated and washed with 20 ml of water. The ether layer is dried over androus sodium sulfate. After evaporation of ether, orange product 90 mg is obtained. Retinal diethyl acetal thus synthesized is identified by infrared spectroscopy, high performance liquid chromatography and thin-layer chromatograph with a mobility of 0.81 on a solvent system of benzene:methanol 1:1.

Retinal diethyl acetal 50 mg synthesized from the above procedure is dissolved in 3 ml of acetone, and the solution thus obtained is mixed with 30 g of petrolatum and 17 g of mineral oil. The composition thus formulated contains 0.1% retinal diethyl acetal as an active ingredient.

EXAMPLE 13

Retinal propylene glycol acetal may be synthesized and formulated in a therapeutic composition as follows.

All-trans retinal 100 mg is dissolved in 10 ml of propylene glycol and 10 ml of ether, and concentrated hydrochloric acid 0.05 ml is added to the mixture with stirring. The reaction mixture changes instantly in color from yellowish to brownish. After 20 minutes at room temperature the mixture is adjusted to alkaline with 0.1 ml of triethanolamine. Ether 10 ml and water 30 ml are added, and the ether layer is separated and washed with 30 ml of water. The ether layer is dried over androus sodium sulfate. After evaporation of ether, orange product 105 mg is obtained. Retinal propylene glycol acetal thus synthesized is identified by infrared spectroscopy, high performance liquid chromatography and thin-layer chromatography with a mobility of 0.80 on a solvent system of benzene:methanol 1:1.

Retinal propylene glycol acetal 50 mg synthesized from the above procedure is dissolved in 3 ml of acetone, and the solution thus obtained is mixed with 47 g of an oil-in-water emulsion. The composition thus formulated contains 0.1% retinal propylene glycol acetal as an active ingredient.

EXAMPLE 14

Retinal 1,2-o-isopropylidene-rac-glyceryl acetal may be synthesized and formulated in a therapeutic composition as follows.

All-trans retinal 100 mg is dissolved in 10 ml of 1,2-o-isopropylidene-rac-glycerol and 5 ml of ether, and concentrated hydrochloric acid 0.02 ml is added to the mixture with stirring. The reaction mixture changes instantly in color from yellowish to orange. After 30 minutes at room temperature the mixture is adjusted to alkaline with 0.1 ml of triethanolamine. Ether 10 ml and water 30 ml are added, and the ether layer is separated and washed with 30 ml of water. The ether layer is dried over androus sodium sulfate. After evaporation of ether, orange product 90 mg is obtained. Retinal 1,2-o-isopropylidene-rac-glyceryl acetal thus synthesized is identified by infrared spectroscopy, high performance liquid chromatography and thin-layer chromatography with a mobility of 0.87 on a solvent system of benzene:methanol 1:1.

Retinal 1,2-o-isopropylidene-rac-glyceryl acetal 50 mg synthesized from the above procedure is dissolved in 3 ml of acetone, and the solution thus obtained is mixed with 47 g of an oil-in-water emulsion. The composition thus formulated contains 0.1% retinal 1,2-o-isopropylidene-rac-glyceryl acetal as an active ingredient.

EXAMPLE 15

Retinal 3-allyloxy-1.2-propanediol acetal may be synthesized and formulated in a therapeutic composition as follows.

All-trans retinal 100 mg is dissolved in 10 ml of 3-allyloxy-1,2-propanediol and 5 ml of ether, and concentrated hydrochloric acid 0.04 ml is added to the mixture with stirring. The reaction mixture changes instantly in color from yellowish to orange. After 30 minutes at room temperature the mixture is adjusted to alkaline with 0.1 ml of triethanolamine. Ether 10 ml and water 30 ml are added, and the ether layer is separated and washed with 30 ml of water. The ether layer is dried over androus sodium sulfate. After evaporation of ether, orange product 82 mg is obtained. Retinal 3-allyloxy-1,2-propanediol acetal thus synthesized is identified by infrared spectroscopy, high performance liquid chromatography and thin-layer chromatography with a mobility of 0.79 on a solvent system of benzene:methanol 1:1.

Retinal 3-allyloxy-1,2-propanediol acetal 50 mg synthesized from the above procedure is dissolved in 3 ml of acetone, and the solution thus obtained is mixed with 30 g of petrolatum and 17 g of mineral oil. The composition thus formulated contains 0.1% retinal 3-allyloxy-1,2-propanediol acetal as an active ingredient.

EXAMPLE 16

Retinal phytyl acetal may be synthesized and formulated in a therapeutic composition as follows.

All-trans retinal 284 mg is dissolved in 1 g of phytol and 20 ml of ether, and concentrated hydrochloric acid 0.05 ml is added to the mixture with stirring. The reaction mixture changes instantly in color from yellowish to orange. After 30 minutes at room temperature the mixture is adjusted to alkaline with 0.1 ml of triethanolamine. Water 40 ml is added, and the ether layer is separated and washed with 40 ml of water. The ether layer is dried over androus sodium sulfate. After evaporation of ether, orange product 350 mg is obtained. Retinal phytyl acetal thus synthesized is identified by infrared spectroscopy, high performance liquid chromatography and thin-layer chromatography with a mobility of 0.72 on a solvent system of benzene:methanol 1:1.

Retinal phytyl acetal 50 mg synthesized from the above procedure is dissolved in 3 ml of acetone, and the solution thus obtained is mixed with 47 g of an oil-in-water emulsion. The composition thus formulated contains 0.1% retinal phytyl acetal as an active ingredient.

EXAMPLE 17

Retinal dibenzyl acetal may be synthesized and formulated in a therapeutic composition as follows.

All-trans retinal 284 mg is dissolved in 1 g of benzyl alcohol and 20 ml of ether, and concentrated hydrochloric acid 0.04 ml is added to the mixture with stirring. The reaction mixture changes instantly in color from yellowish to orange. After 30 minutes at room temperature the mixture is adjusted to alkaline with 0.1 ml of triethanolamine. Water 40 ml is added, and the ether layer is separated and washed with 40 ml of water. The ether layer is dried over androus sodium sulfate. After evaporation of ether, orange product 390 mg is obtained. Retinal dibenzyl acetal thus synthesized is identified by infrared spectroscopy, high performance liquid chromatography and thin-layer chromatography with a mobility of 0.84 on a solvent system of benzene:methanol 1:1.

Retinal dibenzyl acetal 50 mg synthesized from the above procedure is dissolved in 3 ml of acetone, and the solution thus obtained is mixed with 47 g of an oil-in-water emulsion. The composition thus formulated contains 0.1% retinal dibenzyl acetal as an active ingredient.

EXAMPLE 18

Retinal dipentyl acetal may be synthesized and formulated in a therapeutic composition as follows.

All-trans retinal 284 mg is dissolved in 0.5 g of 1-pentanol and 20 ml of ether, and concentrated hydrochloric acid 0.04 ml is added to the mixture with stirring. The reaction mixture changes instantly in color from yellowish to orange. After 30 minutes at room temperature the mixture is adjusted to alkaline with 0.1 ml of triethanolamine. Water 30 ml is added, and the ether layer is separated and washed with 40 ml of water. The ether layer is dried over androus sodium sulfate. After evaporation of ether, orange product 325 mg is obtained. Retinal dipentyl acetal thus synthesized is identified by infrared spectroscopy, high performance liquid chromatography and thin-layer chromatography with a mobility of 0.83 on a solvent system of benzene:methanol 1:1.

Retinal dipentyl acetal 50 mg synthesized from the above procedure is dissolved in 3 ml of acetone, and the solution thus obtained is mixed with 30 g of petrolatum and 17 g of mineral oil. The composition thus formulated contains 0.1% retinal dipentyl acetal as an active ingredient.

EXAMPLE 19

Retinal didodecyl acetal may be synthesized and formulated in a therapeutic composition as follows.

All-trans retinal 284 mg is dissolved in 500 mg of lauryl alcohol and 20 ml of ether, and concentrated hydrochloric acid 0.05 ml is added to the mixture with stirring. The reaction mixture changes instantly in color from yellowish to orange. After 30 minutes at room temperature the mixture is adjusted to alkaline with 0.1 ml of triethanolamine. Water 40 ml is added, and the ether layer is separated and washed with 40 ml of water. The ether layer is dried over androus sodium sulfate. After evaporation of ether, orange product 305 mg is obtained. Retinal didodecyl acetal thus synthesized is identified by infrared spectroscopy, high performance liquid chromatography and thin-layer chromatography with a mobility of 0.78 on a solvent system of benzene:methanol 1:1.

Retinal didodecyl acetal 50 mg synthesized from the above procedure is dissolved in 3 ml of acetone, and the solution thus obtained is mixed with 47 g of an oil-in-water emulsion. The composition thus formulated contains 0.1% retinal didodecyl acetal as an active ingredient.

TEST RESULTS 1. Animal Studies

Preliminary tests were done on hairless mice and rhino mice. A test composition containing various concentrations of retinal or its derivative was topically applied to the left dorsal skin of a mouse and a control vehicle was topically applied to the right dorsal skin of the same mouse. Two mice were used for each test composition, and the topical application was carried out once daily, 5 times a week for 2 weeks. At the end of 2 weeks biopsy specimens were taken from the treated sites and also the untreated sites, and were stained and examined histologically. Microscopic examination of the biopsied skin showed that retinal and its derivatives on topical administration increased the number of granular layers, but decreased the thickness of stratum corneum in the skin of the hairless mice and the rhino mice. In the case of rhino mice, retinal and its derivatives had caused comedone impactions of follicular utriculi to disappear, and seemed to diminish the keratinization in the skin of the rhino mice. The skin from the untreated sites and also the vehicle alone treated sites of hairless mice and rhino mice showed no detectable changes under the same conditions.

2. Wrinkles and Skin Changes Associated with Aging

Therapeutic compositions containing retinal or its derivative with or without hydroquinone as described in Examples were provided to 23 volunteers and patients having age spots, wrinkles, melasma, lentigines or other pigmented skin spots. Each participating subject received two products, i.e. with or without the addition of hydroquinone to the composition containing retinal or its derivative. The volunteers and patients were instructed to apply topically one medication on one side of the body such as on the back of the left hand and the other medication on the other side of the body such as on the back of the right hand. Specific instructions were given to the participating subjects that the medications were applied twice daily to the skin areas or lesions of age spots. Clinical photos were taken of participating subjects before the initiation of the topical treatment and also at the end of each month after the treatment began.

At the end of one month, improvement of age spots was clinically discernible. After two to three months of topical treatment substantial improvement of age spots and fine wrinkles occurred in 19 out of 23 subjects tested. Complete eradication of age spots and fine wrinkles occurred after two to six months of topical administration with compositions containing retinal or its derivative. Deeper wrinkles seemed to take longer time of topical treatment to show any substantial improvement. Therapeutic compositions containing both retinal or its derivative and hydroquinone were judged to be more effective in eradicating pigmented age spots, melasma, lentigines and other pigmented skin spots. With the addition of an alpha hydroxyacid such as glycolic acid, lactic acid and gluconolactone therapeutic compositions containing retinal or its derivative and hydroquinone have been found to be very effective for topical treatment of wrinkles, pigmented or unpigmented age spots, melasma, lentigines and other skin changes associated with aging.

Considering various combination compositions containing retinal and other cosmetic and pharmaceutical agents, the therapeutic composition containing retinal, hydroquinone and an alpha hydroxyacid acid has been found to be one of the most effective formulations for improving wrinkles and the skin changes associated with aging.

3. Skin Cleansing and Oily Skin

Nine human subjects having oily skin or blemished skin as well as 12 acne patients having extremely oily skin participated in this study. Compositions containing retinal or its derivative may be in a form of solution, gel, lotion or cream formulation, but most participants preferred a solution or gel over lotion or cream preparation.

Each participating subject received a solution or a gel preparation containing 0.02 to 0.2% of retinal or its derivative. The participating subjects were instructed to apply topically the solution or gel medication on the affected areas of forehead, face, back and chest. Twice daily administration was continued for 2 to 8 weeks.

The degree of improvement of oily skin as well as the rate of improvement of acne lesions were clinically evaluated. Most participants reported that oiliness of skin disappeared within one to two weeks of topical administration, and the skin so treated became smooth and soft. Two acne patients reported that the solution composition containing 0.2% retinal in water, ethanol and propylene glycol has caused excessive dryness to their skin. However, after they had switched to topical use of 0.05% retinal in a gel preparation the excessive dryness of skin disappeared, and the acne lesions improved substantially. It was found that 18 out of 21 participants showed substantial improvements on oily skin and acne lesions after eight weeks topical administration of therapeutic compositions containing retinal or its derivative.

As a skin cleanser for oily skin or acne-prone skin, the therapeutic composition containing retinal or its derivative may also contain alpha hydroxyacids or other cosmetic and pharmaceutical agents. For example, a therapeutic solution or gel composition containing both retinal and benzilic acid has been found to be one of the most effective compositions for oily skin and acne-prone skin.

4. Acne: Systemic Administration

Therapeutic compositions containing all-trans retinal for oral administration were formulated as gelatin capsules containing from 10 to 25 mg of retinal as an active ingredient. Four acne patients having papulo-pustular or cystic acne participated in this study. Each patient was instructed to take orally one capsule each time, three times daily for 2 to 4 weeks.

Two patients having papulo-pustular lesions of acne were taking daily oral dose of 30 to 50 mg of all-trans retinal. The acne lesions improved substantially after 14 days oral administration of compositions containing all-trans retinal. Two patients having cystic lesions of acne were taking daily oral doses of 75 to 100 mg of all-trans retinal. The acne lesions improved substantially after 2 to 4 weeks oral administration of compositions containing all-trans retinal.

5. Psoriasis

The involved skin in psoriasis is hyperplastic (thickened), erythematous (red or inflamed), and has thick adherent scales. The degree of thickening is such that lesions are elevated up to 1 mm above the surface of adjacent normal skin; erythema is usually an intense red; the thickened adherent scales cause the surface of involved skin to be markedly rough and uneven. These three attributes of thickness, color and texture can be quantified to allow objective measurement of degree of improvement from topically applied test materials or systemically administered medications as follows.

|  | Degree Of Improvement | | | | |
| --- | --- | --- | --- | --- | --- |
|  | None (0) | Mild (1+) | Moderate (2+) | Substantial (3+) | Complete (4+) |
| Thickness | Highly elevated | Detectable reduction | Readily apparent | Barely elevated | Normal thickness |
| Texture | Visibly rough | Palpably rough | Uneven but not | Slightly uneven | Visibly and |
| Color | Intense Red | Red | rough Dark Pink | Light Pink | palpably smooth Normal skin color |

By means of such parameters degree of improvement in psoriatic lesions can be numerically recorded and comparisons made of one treated site to another.

A. Topical Administration

Therapeutic compositions containing 0.05 to 0.2% retinal or its derivative were formulated as lotion, cream or ointment form. Seven patients having psoriasis participated in this study. Each patient was instructed to apply topically the medication in an amount sufficient to cover circles approximately 4 cm in diameter of involved areas of skin. Applications were made two to three times daily and without occlusive dressings. Generally, the involved skin became less scaly and less erythematous after one week of topical treatment. It was found that five out of seven patients showed substantial improvement on the treated areas of skin after two weeks topical application of compositions containing retinal or its derivative.

B. Systemic Administration

Compositions containing all-trans retinal for oral administration were formulated as gelatin capsules containing 25 mg retinal as an active ingredient. Two patients having psoriasis participated in this study. Each patient was instructed to take orally one capsule each time, four times daily for one to two weeks. Both patients shows substantial improvement on psoriatic skin after one week of oral administration. One patient shows a complete clearing of psoriasis lesions after two weeks oral administration of composition containing all-trans retinal with daily does of 2 mg per kg body weight.

6. Warts: Intralesional Injections

Compositions containing 2 mg per ml of all-trans retinal in safflower oil or isopropyl myristate for intralesional injections were sterilized according to a standard procedure. Wart lesions on the hand and plantar warts on the foot were injected intralesionally with the solution containing all-trans retinal. Each wart lesion was injected with 0.02 ml solution, i.e. 0.04 mg of all-trans retinal. The same procedure of treatment was repeated on each wart lesion after one week. At the end of 2 weeks from the initial treatment by intralesional injections most wart lesions became flattened with signs of being eradicated. Some large lesions of warts or more resistant ones showed some signs of improvement after two intralesional injections. It was, however, necessary to repeat the same procedure of treatment a few times more for a complete eradication of wart lesions.

The invention may be embodied in other specific forms without departing from the spirit or essential characteristics thereof. The present embodiments are therefore to be considered in all respects as illustrative and not restrictive, the scope of the invention being indicated by the appended claims and all changes which come within the meaning and equivalency of the claims are therefore intended to be embraced therein.

We claim:

1. A method of alleviating warts, comprising administering topically or by intralesion injection to involved areas of the body a retinal compound having the formula:

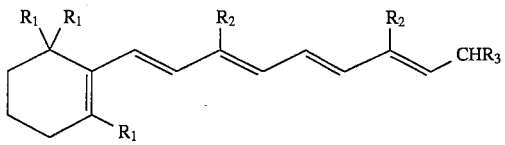

wherein

R₁ and R₂ represent alkyl, cycloalkyl, aralkyl, aryl or alkoxy group of saturated or unsaturated, isomeric or non-isomeric form, having 1 to 25 carbon atoms, provided, however, when R₁ and R₂ represent aralkyl or aryl the number of carbon atoms shall be at least 6 and without fused aromatic rings, R₃ represents O or (OR₄) (OR₅), wherein R₄ and R₅ represent H, alkyl, cycloalkyl, aralkyl or aryl group of saturated or unsaturated, isomeric or non-isomeric form, having 1 to 25 carbon atoms; provided, however, when R₄ and R₅ represent aralkyl or aryl the number of carbon atoms shall be at least 6 and without fused aromatic rings, and the hydrogen atom attached to the carbon atom in the main chain as well as in R₁, R₂, R₄ and R₅ may be substituted by a halogen atom or a lower alkyl or alkoxy radical having 1 to 9 carbon atoms; or stereoisomers thereof in a cosmetically acceptable vehicle.

2. The method according to claim 1, wherein said stereoisomers are selected from the group consisting of all-trans, 13-cis, 11-cis, 9-cis, 7-cis, 11,13-cis and 9,13-cis.

3. The method according to claim 1, wherein the retinal compound is selected from the group consisting of retinal, retinal hydrate, retinal methyl hemiacetal, retinal ethyl hemiacetal, retinal propyl hemiacetal, retinal isopropyl hemiacetal, retinal butyl hemiacetal, retinal pentyl hemiacetal, retinal octyl hemiacetal, retinal benzyl hemiacetal, retinal dimethyl acetal, retinal diethyl acetal, retinal dipropyl acetal, retinal diisopropyl acetal, retinal dibutyl acetal, retinal dipentyl acetal, retinal dioctyl acetal, retinal dibenzyl acetal, retinal propylene glycol hemiacetal, retinal 1,2-o-isopropylidene glyceryl hemiacetal, retinal 3-allyloxy-1, 2-propanediol hemiacetal, retinal phytyl hemiacetal, retinal diphytyl acetal, retinal dodecyl hemiacetal and retinal didoecyl acetal.

4. The method according to claim 3, wherein the retinal compound has the formula:

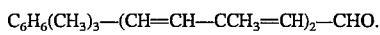

$C_6H_6(CH_3)_3$—$(CH=CH-CCH_3=CH)_2$—CHO.

5. A therapeutic composition for cosmetic or dermatologic skin disorders comprising (A) a retinal compound having the formula:

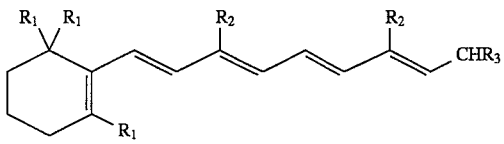

wherein

R₁ and R₂ represent alkyl, cycloalkyl, aralkyl, aryl or alkoxy group of saturated or unsaturated, isomeric or non-isomeric form, having 1 to 25 carbon atoms, provided, however, when R₁ and R₂ represent aralkyl or aryl the number of carbon atoms shall be at least 6 and without fused aromatic rings, R₃ represents O or (OR₄) (OR₅), wherein R₄ and R₅ represent H, alkyl, cycloalkyl, aralkyl or aryl group of saturated or unsaturated, isomeric or non-isomeric form, having 1 to 25 carbon atoms; provided, however, when R₄ and R₅ represent aralkyl or aryl the number of carbon atoms shall be at least 6 and without fused aromatic rings, and the hydrogen atom attached to the carbon atom in the main chain as well as in R₁, R₂, R₄ and R₅ may be substituted by a halogen atom or a lower alkyl or alkoxy radical having 1 to 9 carbon atoms; or stereoisomers thereof;

and (B) an effective amount of a therapeutic, cosmetic or dermatologic agent in a pharmaceutically acceptable vehicle for systemic administration or for topical application to involved body areas.

6. The therapeutic composition of claim 5, wherein said cosmetic and dermatologic disorders include oily-skin, dandruff, age spots, warts, eczema, psoriasis, wrinkles, seborrheic keratoses, xerosis, pruritic skin, disturbed keratinization, inflammatory dermatoses, melasma, lentigines, and pigmented skin spots.

7. The therapeutic composition of claim 5, wherein the retinal compound is a stereoisomers selected from the group consisting of all-trans, 13-cis, 11-cis, 9-cis, 7-cis, 11,13-cis and 9,13-cis.

8. The therapeutic composition of claim 5, wherein the retinal compound is a member selected from the group consisting of retinal, retinal hydrate, retinal methyl hemiacetal, retinal ethyl hemiacetal, retinal propyl hemiacetal, retinal isopropyl hemiacetal, retinal butyl hemiacetal, retinal pentyl hemiacetal, retinal octyl hemiacetal, retinal benzyl hemiacetal, retinal dimethyl acetal, retinal diethyl acetal, retinal dipropyl acetal, retinal diisopropyl acetal, retinal dibutyl acetal, retinal dipentyl acetal, retinal dioctyl acetal, retinal dibenzyl acetal, retinal propylene glycol hemiacetal, retinal 1,2-o-isopropylidene glyceryl hemiacetal, retinal 3-allyloxy-1,2-propanediol hemiacetal, retinal phytyl hemiacetal, retinal diphytyl acetal, retinal dodecyl hemiacetal and retinal didoecyl acetal.

9. The therapeutic composition as claimed in claim 5, wherein the retinal compound has the formula:

$C_6H_6(CH_3)_3$—$(CH=CH-CCH_3=CH)_2$—CHO.

10. The therapeutic composition as claimed in claim 5, wherein said cosmetic and dermatologic agents are selected from the group consisting of antiwrinkle, antikeratosis, antiagespot, antiacne, antidandruff, antipruritic, antibacterial, antiyeast, antiviral, antidermatitis, antiinflammatory, antihyperkeratotic, antixerosis, antipsoriasis, antipigmenting and antihistamine agents; sunscreen agents; local anesthetics; vitamins; corticosteroids; 5-fluorouracil; retinoids; retinoic acid; retinyl palmitate; monobenzone; hydroquinone, clotrimazole; miconazole; ketoconazole; pramoxine; salicylic acid; menthol; hydrocortisone; hydrocortisone valerate; betamethasone valerate; betamethasone dipropionate; triamcinolone acetonide; fluocinonide; clobetasol propionate; benzoyl peroxide; crotamiton; vitamin E acetate and vitamin C.

11. A method of improving cosmetic or dermatologic skin disorders comprising administering systemically or topically to involved areas a composition comprising (A) a retinal compound having the formula:

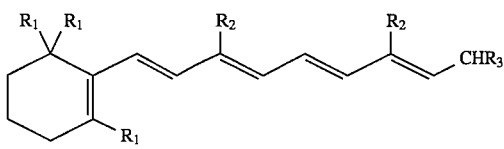

wherein

- $R_1$ and $R_2$ represent alkyl, cycloalkyl, aralkyl, aryl or alkoxy group of saturated or unsaturated, isomeric or non-isomeric form, having 1 to 25 carbon atoms, provided, however, when $R_1$ and $R_2$ represent aralkyl or aryl the number of carbon atoms shall be at least 6 and without fused aromatic rings,
- $R_3$ represents O or $(OR_4)(OR_5)$, wherein $R_4$ and $R_5$ represent H, alkyl, cycloalkyl, aralkyl or aryl group of saturated or unsaturated, isomeric or non-isomeric form, having 1 to 25 carbon atoms; provided, however, when $R_4$ and $R_5$ represent aralkyl or aryl the number of carbon atoms shall be at least 6 and without fused aromatic rings, and the hydrogen atom attached to the carbon atom in the main chain as well as in $R_1$, $R_2$, $R_4$ and $R_5$ may be substituted by a halogen atom or a lower alkyl or alkoxy radical having 1 to 9 carbon atoms; or stereoisomers thereof;
- and (B) an effective amount of a therapeutic, cosmetic or dermatologic agent in a pharmaceutically acceptable vehicle for systemic administration or for topical application to involved body areas.

12. The method as claimed in claim 11, wherein said cosmetic and dermatologic disorders include oily-skin, dandruff, age spots, warts, eczema, psoriasis, wrinkles, seborrheic keratoses, xerosis, pruritic skin, disturbed keratinization, inflammatory dermatoses, melasma, lentigines, and pigmented skin spots.

13. The method as claimed in claim 11, wherein the retinal compound is a stereoisomers selected from the group consisting of all-trans, 13-cis, 11-cis, 9-cis, 7-cis, 11,13-cis and 9,13-cis.

14. The method as claimed in claim 11, wherein the retinal compound is a member selected from the group consisting of retinal, retinal hydrate, retinal methyl hemiacetal, retinal ethyl hemiacetal, retinal propyl hemiacetal, retinal isopropyl hemiacetal, retinal butyl hemiacetal, retinal pentyl hemiacetal, retinal octyl hemiacetal, retinal benzyl hemiacetal, retinal dimethyl acetal, retinal diethyl acetal, retinal dipropyl acetal, retinal diisopropyl acetal, retinal dibutyl acetal, retinal dipentyl acetal, retinal dioctyl acetal, retinal dibenzyl acetal, retinal propylene glycol hemiacetal, retinal 1,2-o-isopropylidene glyceryl hemiacetal, retinal 3-allyloxy-1,2-propanediol hemiacetal, retinal phytyl hemiacetal, retinal diphytyl acetal, retinal dodecyl hemiacetal and retinal didoecyl acetal.

15. The method as claimed in claim 11, wherein the retinal compound has the formula:

$$C_6H_6(CH_3)_3-(CH=CH-CCH_3=CH)_2-CHO.$$

16. The method as claimed in claim 11, wherein said cosmetic and dermatologic agents are selected from the group consisting of antiwrinkle, antikeratosis, antiagespot, antiacne, antidandruff, antipruritic, antibacterial, antiyeast, antiviral, antidermatitis, antiinflammatory, antihyperkeratotic, antixerosis, antipsoriasis, antipigmenting and antihistamine agents; sunscreen agents; local anesthetics; 5-fluorouracil; retinoids; retinoic acid; retinyl palmitate; monobenzone; hydroquinone, clotrimazole; miconazole; ketoconazole; pramoxine; salicylic acid; menthol; hydrocortisone; hydrocortisone valerate; betamethasone valerate; betamethasone dipropionate; triamcinolone acetonide; fluocinonide; clobetasol propionate; benzoyl peroxide; crotamiton; vitamin E acetate and vitamin C.

\* \* \* \* \*